Figure 1:
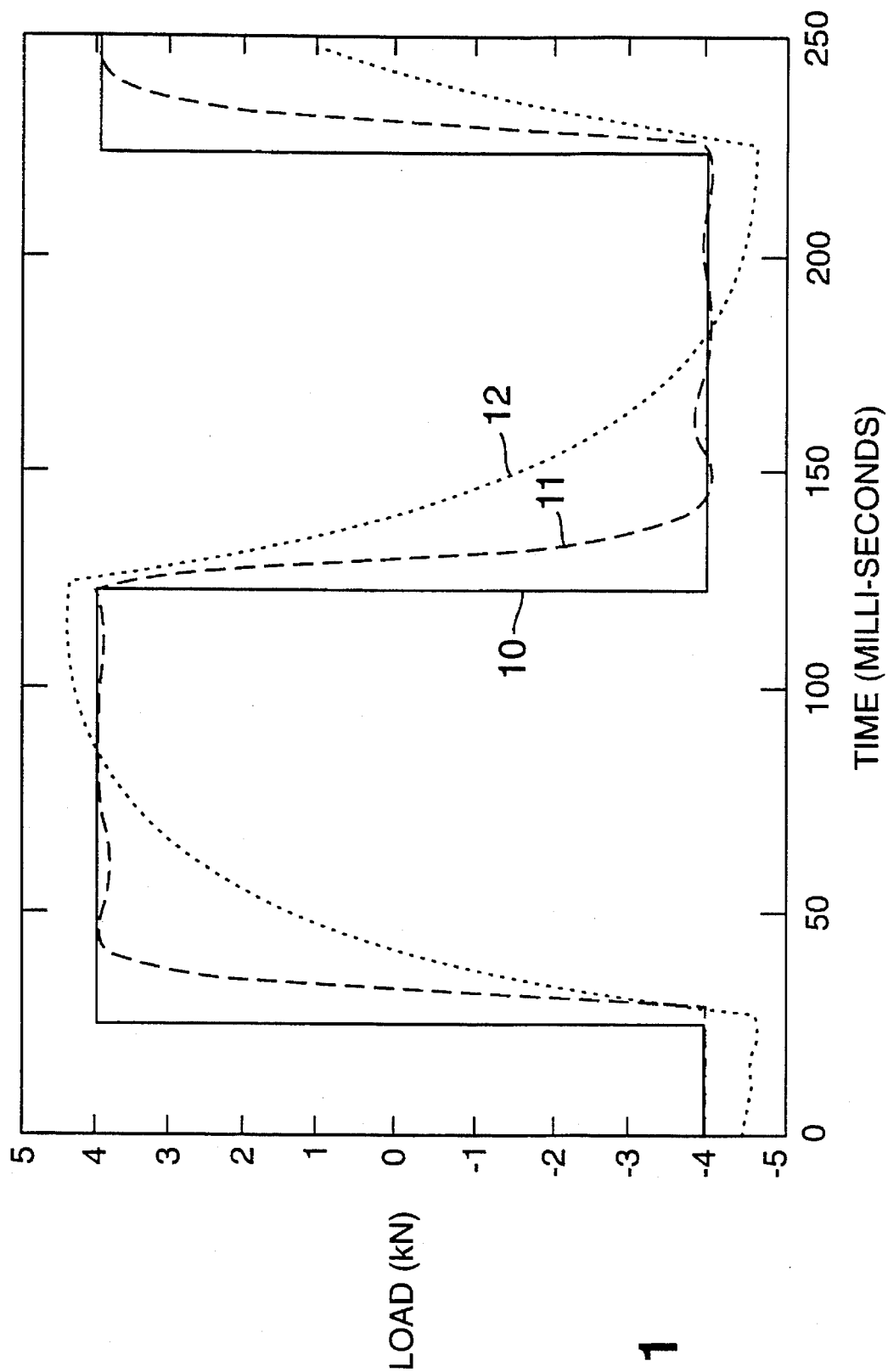

United States Patent [19]
Hinton

[11] Patent Number: 5,511,431
[45] Date of Patent: Apr. 30, 1996

[54] STRUCTURE TESTING MACHINE

[75] Inventor: Christopher E. Hinton, Wheatley, United Kingdom

[73] Assignee: Instron Limited, Buckinghamshire, United Kingdom

[21] Appl. No.: 310,871

[22] Filed: Sep. 23, 1994

[30] Foreign Application Priority Data

Sep. 24, 1993 [GB] United Kingdom .................. 9319788

[51] Int. Cl.$^6$ ........................................................ G01N 3/00
[52] U.S. Cl. ................................................ 73/806; 73/805
[58] Field of Search ............................. 73/816, 763, 805, 73/806, 837

[56] References Cited

U.S. PATENT DOCUMENTS

| | | | |
|---|---|---|---|
| 3,304,768 | 2/1967 | Naumann | 73/816 |
| 4,003,246 | 1/1977 | Cain | 73/805 |
| 4,235,114 | 11/1980 | Mohler | 73/805 |
| 4,802,367 | 2/1989 | Petersen et al. | 73/805 |

FOREIGN PATENT DOCUMENTS 2205959  12/1988  United Kingdom .

*Primary Examiner*—Richard Chilcot
*Assistant Examiner*—Max H. Noori
*Attorney, Agent, or Firm*—Fish & Richardson

[57] ABSTRACT

A structure testing machine for carrying out tests on a test structure (25) for an assessment of the response of the structure to test loads applied to the structure in the direction of a predetermined axis of the structure under the control of a monitored control system (21) which forms part of the machine and which has a forward path which includes an actuator (24) which is supported by a machine frame and which upon actuation applies to the test structure a test load in the direction of the predetermined axis, and a controller (22) responsive to a controller input signal and to controller parameters to apply to the actuator an actuating signal to cause the actuator to subject the test structure to a test load which produces dimensional changes in the test structure in the direction of the predetermined axis. The machine is provided with an adaptive control loop which comprises a stiffness estimator (27) which generates from the dimensional changes in the test structure adaptive control signals ($E_S$) representative of the structure stiffness and adaptive control signals ($E_C$) representative of the combined stiffness of the actuator, actuator support frame and the test structure, and means (30) to update the controller parameters of the controller to modify the forward path gain of the controller in response to the adaptive control signals thereby to adapt the machine to changes in the stiffness of the test structure relative to the combined stiffness of the machine and the test structure.

10 Claims, 4 Drawing Sheets

STRUCTURE TESTING MACHINE

The present invention relates to structure testing machines for carrying out tests on a test structure for an assessment of the response of the structure to test loads applied to the structure.

The structure to be tested may be a test specimen and the machine a materials testing machine for carrying out materials testing on the specimen to provide an assessment of one or more of the physical properties of the specimen material.

Alternatively the structure may be a test component and the machine adapted for carrying out tests on the test component for an assessment of the response of the component to test loads applied to the component.

In materials testing machines, test loads are applied to a test specimen in the direction of a predetermined axis of the specimen under the control of a monitored control system which forms part of the machine and which has a forward path which includes an actuator which is supported by a machine frame and which upon actuation applies to the test specimen a test load in the direction of a predetermined axis of the test specimen and a controller responsive to a controller input signal and to controller parameters to apply to the actuator an actuating signal to cause the actuator to subject the test specimen to a test load which produces dimensional changes in the test specimen in the direction of the predetermined axis.

In materials testing machines the monitored control system normally used is a closed loop system which includes a feedback path for feeding back condition signals representative of a predetermined condition of the test specimen as a result of the application of a controller input signal to the controller and a comparator responsive to an input demand signal and the condition signal to generate a controller input signal representative of the difference between the input demand signal and the condition signal.

The controller normally takes the form of a PID controller in which the demand signal is a signal demanding a predetermined position of, load on or extension of the test specimen and the feedback path includes a mode selection unit for feeding back condition signals representative of the position of, load on or extension of the test specimen.

While such materials testing machines have been used for many years, it is recognised that their performance is lacking in some respects. In particular, the dynamic behaviour of such materials testing machines is affected by the stiffness of the test specimen. Sensitivity to specimen stiffness poses two problems. Firstly, the machine controller has to be re-tuned every time a different type of specimen is loaded. Currently such retuning is done manually and because this requires some skill, is sometimes done badly. Secondly, even if the machine controller is correctly tuned at the start of a test, stiffness changes during the test prevent optimum performance being maintained. Such stiffness changes are common. In metals testing, for example, damage mechanisms such as the propagation of fatigue cracks or transitions from elastic to plastic behaviour cause the stiffness to change. Other specimens—like automotive elastomeric components—have an inherently non-linear stiffness characteristic.

How a stiffness change affects the testing machine depends upon the mode of control used for the test. In load-control, response becomes more sluggish as the stiffness of the specimen reduces. In strain-control the reverse happens; response becomes sharper but this can lead to closed-loop instability.

Sensitivity to stiffness change depends on the fixed stiffness of the hydraulic actuator and load-frame. The load-frame is designed to be stiff to minimise the strain energy stored when the specimen is loaded. Actuators, on the other hand, come in all shapes and sizes to suit varied requirements of speed, force and stroke. Sensitivity is worst in load control if the actuator is stiff. In strain control, machines fitted with soft actuators tend to be most affected.

A self-optimising PID controller has been proposed for use with machines having slowly or discontinuously varying parameters. The controller uses an impulse signal to determine system dynamics. A hill-climbing optimisation routine is then employed to find the best set of PID parameters. The method is principally aimed at initial auto-tuning. It has been suggested that it could be used during testing to re-tune the controller but this would involve applying more impulse signals.

It has also been proposed to provide a control and monitoring system for a servo-hydraulic fatigue testing machine which uses a computer network with adaptive control of amplitude and frequency. This is an outerloop control system for improving the turning point accuracy of variable amplitude loading during fatigue testing. It is a learning controller which makes demand signal adjustments based upon the errors recorded the last time the test sequence was applied. It only looks at turning point accuracy. Traverses from one turning point to the next are not monitored. Only the demand signal is modified. The fidelity of the primary feedback loop remains uncorrected.

Various self-tuning control systems for closed loop servo hydraulic materials testing machines have also been proposed. In one proposal the stated aim was to provide a self-tuning controller for servo-hydraulic materials testing machines which did not have to be manually tuned by the sort of trial and error approach used on existing PID controllers. After several investigations, a pole-placement controller was adopted. Trials revealed that the system worked well as long as the demand signal was dynamically rich.

Repetitive control systems using a regeneration spectrum and developed for systems with periodic inputs have been applied to materials testing. This is however another learning type of controller which cycle by cycle reduces errors caused by non-linearities. It is however only suitable for periodic waveforms.

The above systems applied as proposed can be classified as self-tuning or learning type controllers. A disadvantage of the learning type controller is that it is specific to particular demand signals and types of test and to extend the self-tuning controller to cope with stiffness changes requires the use of unwanted probing signals to estimate dynamics. Estimation is particularly difficult in materials testing where normal operating signals are often not dynamically rich and where probing cannot be tolerated during many material tests.

It is an object of the present invention to provide in a structure testing machine a monitored control system which adapts the machine to changes in the stiffness of the test structure but which does not suffer from the above-mentioned disadvantages of the hitherto proposed self-tuning and learning-type controllers.

According to the present invention there is provided a structure testing machine for carrying out tests on a test structure for an assessment of the response of the structure to test loads applied to the structure in the direction of a predetermined axis of the structure under the control of a monitored control system which forms part of the machine and which has a forward path which includes an actuator which is supported by a machine frame and which upon actuation applies to the test structure a test load in the direction of the predetermined axis, and a controller responsive to a controller input signal and to controller parameters to apply to the actuator an actuating signal to cause the actuator to subject the test structure to a test load which produces dimensional changes in the test structure in the direction of the predetermined axis, characterised by the provision of an adaptive control loop which comprises a stiffness estimator which generates from the dimensional changes in the test structure adaptive control signals representative of the structure stiffness and adaptive control signals representative of the combined stiffness of the actuator, actuator support frame and the test structure, and means to update the controller parameters of the controller to modify the forward path gain of the controller in response to the adaptive control signals thereby to adapt the machine to changes in the stiffness of the test structure relative to the combined stiffness of the machine and the test structure.

In an embodiment of the invention hereinafter to be described the monitored control system is a closed loop system which includes a feedback path for feeding back condition signals representative of a predetermined condition of the test structure as a result of the application of a control input signal to the controller and comparison means responsive to an input demand signal and the condition signal to generate a controller input signal representative of the difference between the input demand signal and the condition signal.

In an embodiment of the invention hereinafter to be described the controller is a PID controller, the demand signal is a signal demanding a predetermined position of, load on or extension of the test structure and the feedback path includes a mode selection unit for feeding back condition signals representative of the position of, load on or extension of the test structure.

In an embodiment of the invention hereinafter to be described the adaptive control loop includes a machine model which provides a mathematical representation of the machine and which generates machine model parameters, and a controller design responsive to test specification inputs applied thereto and representative of predetermined alternative tests to modify the model parameters and to generate updating controller parameters.

In an embodiment of the invention hereinafter to be described the structure to be tested is a test specimen and the machine is a materials testing machine for carrying out materials testing on the test specimen to provide an assessment of one or more of the physical properties of the specimen material under test loads applied to the specimen in the direction of the predetermined axis. In the specific embodiments of the invention hereinafter to be described, the machine is a servo-hydraulic testing machine and the actuator is a hydraulic actuator.

In an alternative embodiment of the invention the machine is an electro-mechanical testing machine and the actuator is a rotary or linear electric motor.

In an alternative embodiment of the invention, the test structure to be tested is a test component and the machine is a component testing machine for carrying out tests on the test component for an assessment of the response of the component to test loads applied thereto in the direction of the predetermined axis.

In another embodiment of the invention the machine additionally or alternatively provides for carrying out tests on a test structure for an assessment of the response of the structure to amplitude varying test loads of high frequency. The machine then further comprises means to store measured stiffness values together with their corresponding time or position or load or strain values and to make a predictive correction to the adaptive control signals generated by the stiffness estimator to compensate for the delay in the response of the estimator and the machine to changes in test structure stiffness during subsequent test load cycles.

In yet another embodiment of the invention the machine according to the invention is employed for carrying out tests on a test component for an assessment of the response of the component to test loads applied to the component in the direction of the predetermined axis of the component and in the direction of a further predetermined axis or in the direction of each of a plurality of further predetermined axes and the machine includes a monitored control system for applying test loads in the direction of each of the predetermined axes.

Figure 2:
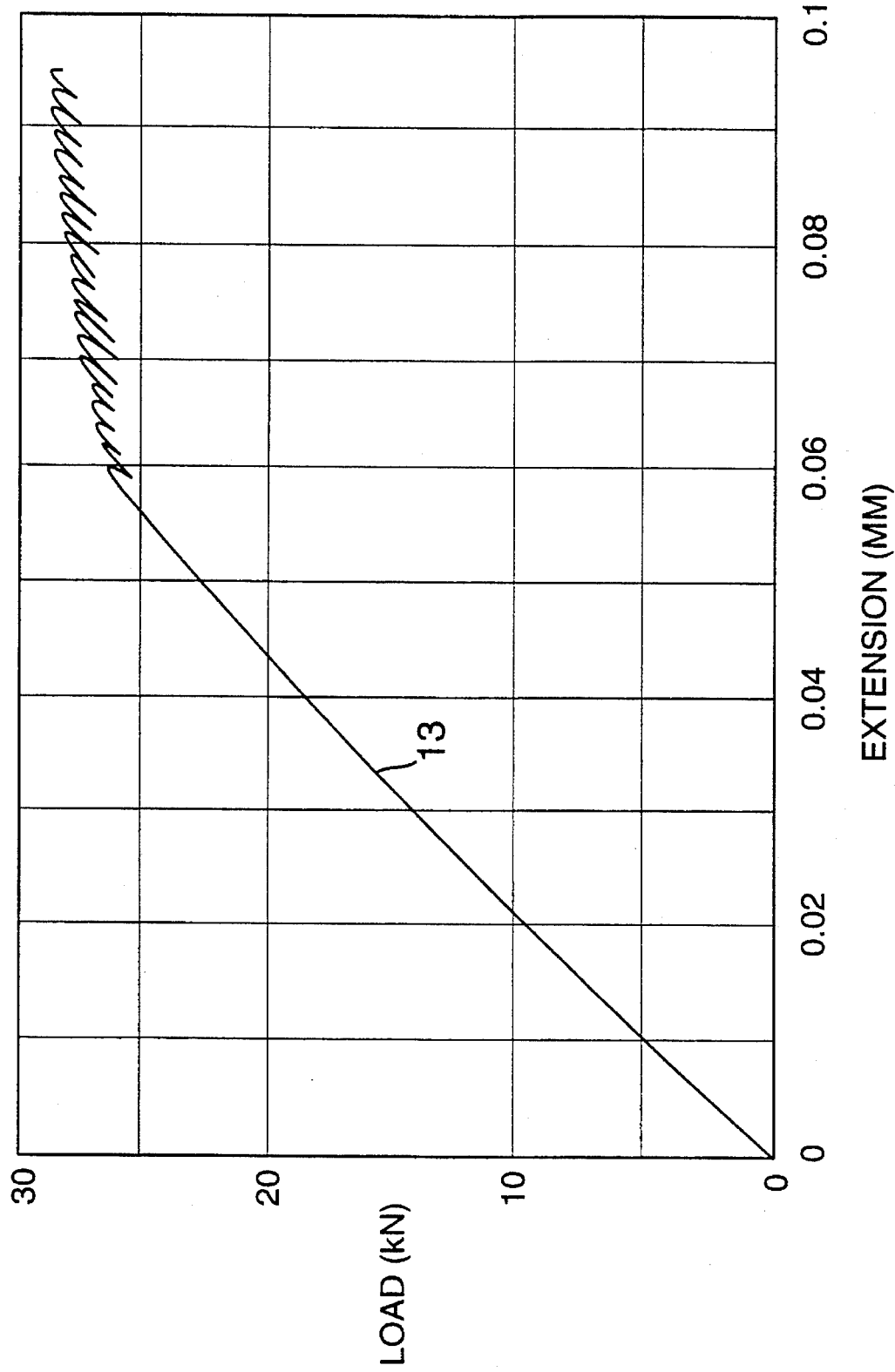
Figure 3:
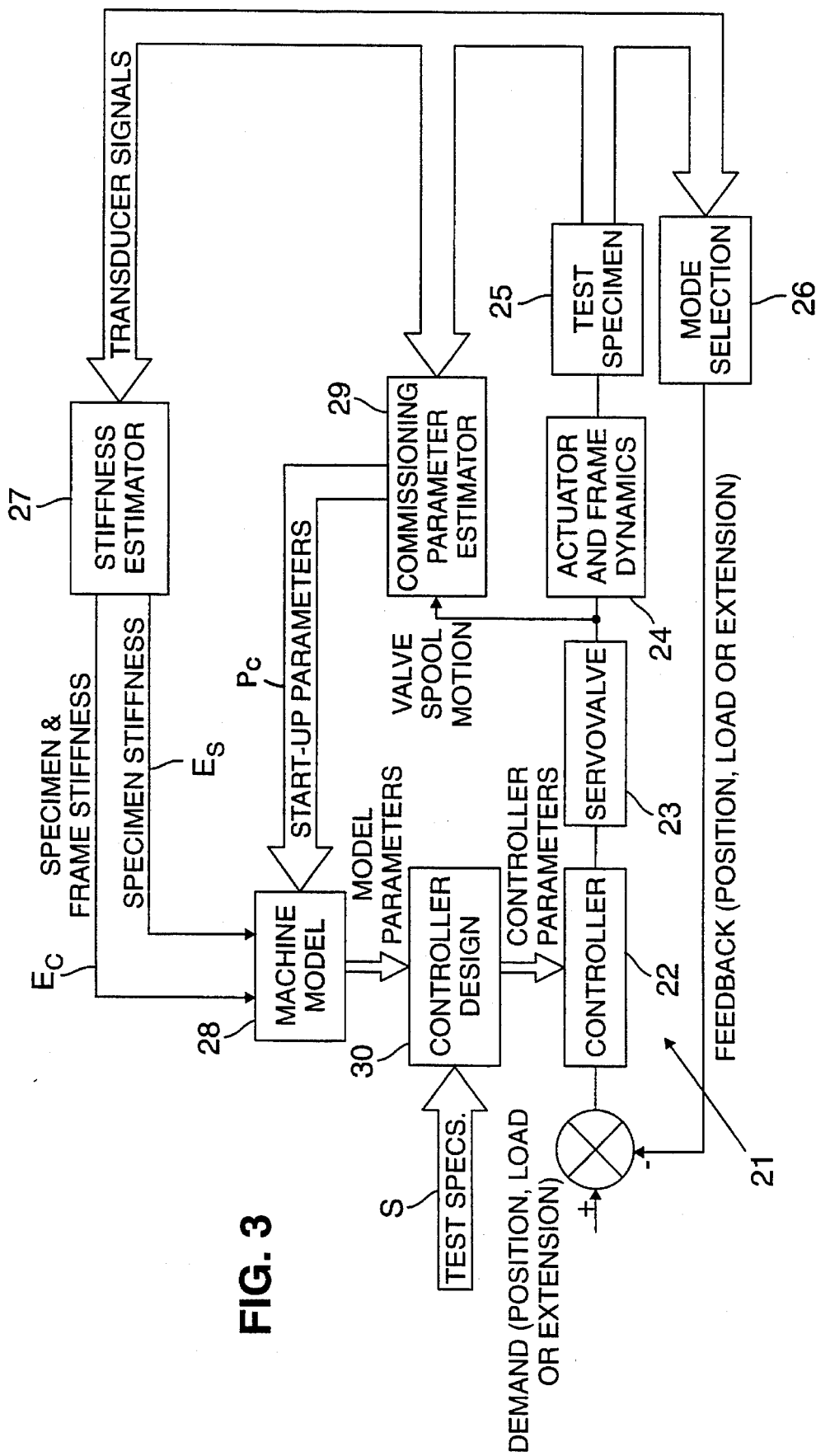
Figure 4:
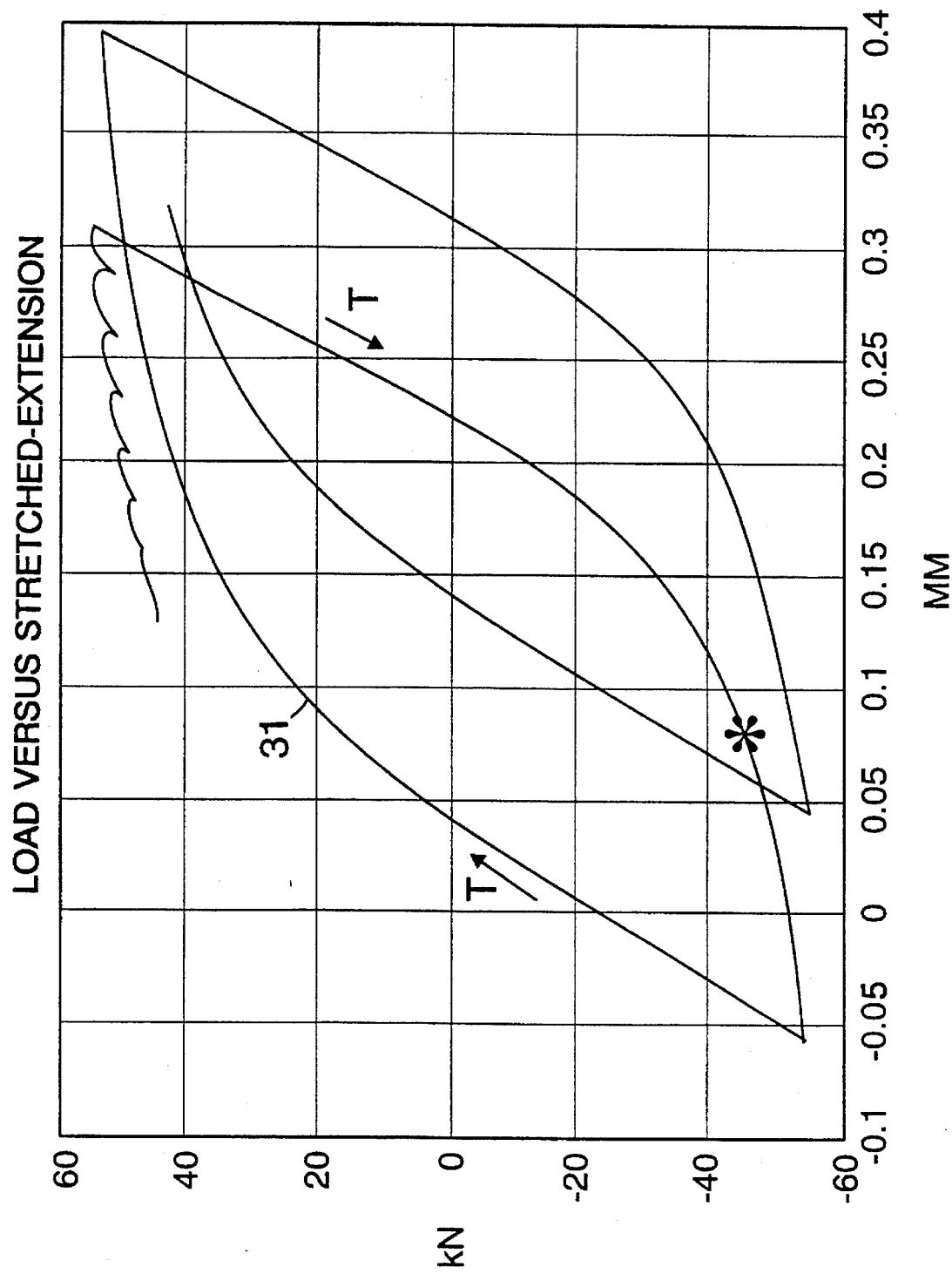

Embodiments of the invention will now be described by way of example with reference to the accompanying drawings in which:

FIG. 1 is a graphical representation illustrating the sensitivity of a material testing machine to specimen stiffness when operated under the control of a conventional PID controller in a load-control mode FIG. 2 is a graphical representation illustrating the instability of a materials testing machine employing a conventional PID controller in a strain-control mode FIG. 3 is a schematic block diagram of a servo-hydraulic materials testing machine according to the invention, and FIG. 4 is a graphical representation illustrating the stability achieved in a low cycle fatigue test carried out on a test specimen by the materials testing machine shown in FIG. 3.

Sensitivity of a materials testing machine to specimen stiffness when operated under the control of a conventional PID controller operating in a load-control mode is illustrated in FIG. 1. The input demand signal is a 5 Hz square wave represented by the solid line 10 and the responses to this input demand signal are shown by the dashed line 11 for a stiff specimen when placed under test and by the dotted line 12 for a soft specimen when placed under test. As shown, the response becomes more sluggish as the stiffness of the specimen reduces.

The instability of a materials testing machine employing a conventional PID controller operating in a strain-control mode is illustrated in FIG. 2. The solid line 13 represents the extension of a test specimen in response to increasing load and shows the effects of closed loop instability resulting from loop gain increases when the specimen yields in the plastic region of the material.

The materials testing machine according to the invention and as now to be described with reference to FIGS. 3 and 4 is, in contrast, made insensitive or substantially insensitive to specimen stiffness changes, whereby the adverse effects described with reference to FIGS. 1 and 2 can be avoided or at least substantially alleviated.

Referring now to FIG. 3 of the accompanying drawings, a schematic block diagram of a materials testing machine according to the invention is shown. In the lower part of the block diagram is a normal feedback control loop 21 consisting of a controller 22, a servo-valve 23, a hydraulic actuator 24 and a test specimen 25. Control mode (position, load or strain) is selected by a mode selection switch 26 which chooses an appropriate feedback signal from transducer signals.

Adaptive control is achieved by modifying the PID controller terms according to real-time estimates $E_S$ of the specimen stiffness and real time estimates $E_C$ of the combined stiffness of the specimen and frame. These estimates $E_S$ and $E_C$ are obtained from the position, load and extension signals by a stiffness estimator 27 shown at the top of the FIG. 3 block diagram.

The relationship between the PID terms and stiffness is not the same on all machines. The relationship for a particular machine is defined by a machine-model 28. This represents mathematically the current dynamics of the actuator, load frame and specimen combination. Its parameters are constituted from the two time-varying stiffness estimates $E_S$ and $E_C$ plus time-invariant terms called machine commissioning start-up parameters $P_C$ which, although fixed, are different from machine to machine.

The start up parameters $P_C$ are determined in a once-only experiment by a commissioning parameter estimator 29 when the machine is first built. Small amplitude square-wave signals are used to perturb the actuator 24 so that these fixed terms can be identified. During subsequent operation, the machine-model 28 only needs to be updated by the stiffness estimates $E_S$ and $E_C$ to accurately reflect any changes in machine dynamics.

A controller design stage 30 is the part of the adaptive control loop which actually changes the PID terms. It does this according to a test specification S using information about the machine-model 28. The requirement for most tests is that the loop gain should be as high as possible without producing significant square-wave response overshoots.

Adaptive control makes the testing machine insensitive or substantially insensitive to stiffness changes in the test specimen 25. Performance is maintained as it was when the system was first commissioned. This is demonstrated by a low cycle fatigue (LCF) test result shown in FIG. 4 of the accompanying drawings.

Referring now to FIG. 4, the graphical representation shown illustrates the stability achieved in a low cycle fatigue test carried out on the test specimen 25 by the materials testing machine shown in FIG. 3. In the test, the test specimen is subjected to cyclically applied test loads, the amplitudes of which exceed the elastic limit of the material during each cycle. The test thus produces in each cycle both elastic and plastic strain. The stiffness of the test specimen is therefore continually changing with abrupt changes at each strain reversal.

The results shown in FIG. 4 arise from tests conducted in strain-control mode at a frequency of 1 Hz. The curve 31 is a plot of the applied load against the extension of the specimen under elastic and plastic strain. The two cycles of the curve 31 have been artificially stretched in the strain direction when plotted so that they can be separated. The two loops would otherwise be superimposed. Increasing time is indicated by the arrows T.

At the start of the test plot the adaptive control is switched off. As a result, oscillations are clearly seen in curve 31 as the initial cycle progresses into the plastic region. These oscillations are caused for the same reason as the oscillations shown in FIG. 2, namely, that in strain control the loop gain increases when the specimen yields. The adaptive control loop is then switched on at the point in curve 31 marked with an asterix, with the result that the oscillations disappeared in the next test load cycle. This demonstrates the effectiveness of the adaptive control loop in the machine according to the invention. Such oscillations in the plastic region have hitherto often frustrated LCF testing. Without adaptive control in accordance with the invention, they can often only be prevented by reducing the controller gain. Such action though has the bad side-effect of degrading performance when the test specimen is elastic and at strain turn around.

The adaptive control loop of the machine described with reference to FIG. 3 can conveniently be made to run on the Assignee's 8500 PLUS direct digital controller currently employed in servo-hydraulic materials testing machines manufactured by them. This is a multi-processor platform. Code resides in firmware. Real-time tasks such as stiffness estimation, the PID controller and PID updates are performed by a TMS320C31 floating-point arithmetic processor and logic unit. Non real-time tasks such as determining the start-up parameters are performed by a MC68340 32-bit cpu with peripheral devices.

In contrast to the control systems hitherto proposed, the control system with its adaptive control loop as hereinbefore described with reference to FIG. 3 has the following advantages:

1. A tuning experiment is not required every time a different type of test specimen is loaded in the testing machine. The machine operator simply loads the new specimen and, without applying any special signals, the adaptive algorithm makes the necessary changes to the controller.

2. Stiffness changes that occur during a test are compensated for without the use of probing signals. This is possible even when the test signals are not dynamically rich.

3. Rapid stiffness changes can be tracked more responsively.

The above advantages stem from the fact that a physical model of the testing machine is used to formulate the adaptive algorithm. This means that only the parameter that is changing i.e. stiffness has to be estimated online. The prior proposals follow the classic black-box approach where reasonable dynamic order is the only structural information that is pre-specified. The physics that govern machine behaviour are completely ignored. This is why response under such control tends to be slow and probing is required if the normal operating signals are not very dynamic.

The servo-hydraulic materials testing machine described with reference to FIG. 3 is one in which the test loads are applied to the specimen in a single direction along a predetermined axis of the specimen. It will however be appreciated that the adaptive control loop forming part of the control system described with reference to FIG. 3 can be applied equally well to other structure testing machines such as those which provide for the testing of test components in a multi axis rig where an assessment needs to be made of the response of the component to test loads applied to the component in two or more predetermined axes of the component. In these circumstances, the structure testing machine would be arranged to include a monitored control system for each of the plurality of predetermined axes and having an adaptive control loop according to the invention.

It will be appreciated by those versed in the art that the adaptive control loop according to the invention can also be applied to electro-mechanical materials testing machines.

While in the description of the materials testing machine illustrated in FIG. 3, reference has been made to low cycle fatigue testing, provision can be made to make it suitable for high frequency testing. Delays in the response of the stiffness estimater and the machine are a problem in high frequency testing and in accordance with another aspect of the invention the machine described with reference to FIG. 3 is modified by the inclusion of means to store measured stiffness values together with their corresponding time or position or load or strain values and to make a predictive correction to the adaptive control signals $E_S$ and $E_C$ generated by the stiffness estimator 27 to compensate for the delay in the response of the estimator 27 and the machine to changes in specimen stiffness during subsequent test load cycles.

I claim:

1. A structure testing machine for carrying out, on a test structure, a cyclic loading test which requires applying to the structure in the direction of a predetermined axis of the structure a cyclic amplitude varying test load which cyclically passes through a reference test load amplitude between a first test load amplitude which is positive relative to the reference test load amplitude and a second test load amplitude which is negative relative to the reference test load amplitude under the control of a monitored control system which forms part of the machine and which has a forward path which includes an actuator which is supported by a machine frame and which upon actuation applies to the test structure the cyclic amplitude varying test load in the direction of the predetermined axis, and a controller responsive to a controller input signal and to controller parameters to apply to the actuator an actuating signal to cause the actuator to subject the test structure to the cyclic amplitude varying test load which produces dimensional changes in the test structure in the direction of the predetermined axis, characterized by the provision of an adaptive control loop which comprises a stiffness estimator which generates, from the dimensional changes in the test structure, adaptive control signals representative of the structure stiffness and adaptive control signals representative of the combined stiffness of the actuator, actuator support frame and the test structure, and further characterized by the provision of means which in response to the adaptive control signals update the controller parameters of the controller to modify the forward path gain of the controller to make the machine dynamics at least substantially insensitive to changes in the stiffness of the test structure relative to the combined stiffness of the machine and the test structure.

2. A machine according to claim 1, wherein the monitored control system is a closed loop system which includes a feedback path for feeding back condition signals representative of a predetermined condition of the test structure as a result of the application of a control input signal to the controller and comparison means responsive to an input demand signal and the condition signal to generate a controller input signal representative of the difference between the input demand signal and the condition signal.

3. A machine according to claim 2, wherein the controller is a PID controller, wherein the demand signal is a signal demanding a predetermined position of, load on or extension of the test structure and wherein the feedback path includes a mode selection unit for feeding back condition signals representative of the position of, load on or extension of the test structure.

4. A structure testing machine for carrying out tests on a test structure for an assessment of the response of the structure to test loads applied to the structure in the direction of a predetermined axis of the structure under the control of a monitored control system which forms part of the machine and which has a forward path which includes an actuator which is supported by a machine frame and which upon actuation applies to the test structure a test load in the direction of the predetermined axis, and a controller responsive to a controller input signal and to controller parameters to apply to the actuator an actuating signal to cause the actuator to subject the test structure to a test load which produces dimensional changes in the test structure in the direction of the predetermined axis, characterized by the provision of an adaptive control loop which comprises a stiffness estimator which generates from the dimensional changes in the test structure adaptive control signals representative of the structure stiffness and adaptive control signals representative of the combined stiffness of the actuator, actuator support frame and the test structure, and means to update the controller parameters of the controller to modify the forward path gain of the controller in response to the adaptive control signals thereby to adapt the machine to changes in the stiffness of the test structure relative to the combined stiffness of the machine and the test structure, the monitored control system being a closed loop system which includes a feedback path for feeding back condition signals representative of a predetermined condition of the test structure a result of the application of a control input signal to the controller and comparison means responsive to an input demand signal and the condition signal to generate a controller input signal representative of the difference between the input demand signal and the condition signal, and the adaptive control loop including a machine model which provides a mathematical representation of the machine and which generates machine model parameters, and a controller design responsive to test specification inputs applied thereto and representative of predetermined alternative tests to modify the model parameters and to generate updating controller parameters.

5. A machine according to claim 1, wherein the structure to be tested is a test specimen and wherein the machine is a materials testing machine to carry out materials testing on the test specimen to provide an assessment of one or more of the physical properties of the specimen material under test loads applied to the specimen in the direction of the predetermined axis.

6. A machine according to claim 1, wherein the test structure to be tested is a test component and wherein the machine is a component testing machine to carry out tests on the test component for an assessment of the response of the component to test loads applied thereto in the direction of the predetermined axis.

7. A machine according to claim 6 for carrying out tests on a test component for an assessment of the response of the component to test loads applied to the component in the direction of the predetermined axis of the component and in the direction of a further predetermined axis or in the direction of each of plurality of further predetermined axes and wherein the machine includes a monitored control system for applying test loads in the direction of each of the predetermined axes.

8. A structure testing machine for carrying out tests on a test structure for an assessment of the response of the structure to amplitude varying test loads of high frequency applied to the structure in the direction of a predetermined axis of the structure under the control of a monitored control system which forms part of the machine and which has a forward path which includes an actuator which is supported by a machine frame and which upon actuation applies to the test structure a test load in the direction of the predetermined axis, and a controller responsive to a controller input signal and to controller parameters to apply to the actuator an actuating signal to cause the actuator to subject the test structure to a test load which produces dimensional changes in the test structure in the direction of the predetermined axis, characterized by the provision of an adaptive control loop which comprises a stiffness estimator which generates from the dimensional changes in the test structure adaptive control signals representative of the structure stiffness and adaptive control signals representative of the combined stiffness of the actuator, actuator support frame and the test structure, and means to update the controller parameters of the controller to modify the forward path gain of the controller in response to the adaptive control signals thereby to adapt the machine to changes in the stiffness of the test structure relative to the combined stiffness of the machine and the test structure, the machine further comprising means to store measured stiffness values together with their corresponding time or position or load or strain values and to make a predictive correction to the adaptive control signals generated by the stiffness estimator to compensate for the delay in the response of the estimator and the machine to changes in test structure stiffness during subsequent test load cycles.

9. A machine according to claim 1, wherein the machine is an electro-mechanical testing machine and the actuator is a rotary or linear electric motor.

10. A machine according to claim 1, wherein the machine is a servo-hydraulic testing machine and the actuator is a hydraulic actuator.

* * * * *